US00PP34949P2

(12) United States Plant Patent
Bacon et al.

(10) Patent No.: US PP34,949 P2
(45) Date of Patent: Jan. 31, 2023

(54) NECTARINE TREE NAMED 'SUNECT30'

(50) Latin Name: ***Prunus persica* var. *nucipersica***
Varietal Denomination: Sunect30

(71) Applicant: Sun World International, LLC, Bakersfield, CA (US)

(72) Inventors: Terry A. Bacon, Bakersfield, CA (US); Terrence J. Frett, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 17/858,338

(22) Filed: Jul. 6, 2022

Related U.S. Application Data

(60) Provisional application No. 63/285,220, filed on Dec. 2, 2021.

(51) Int. Cl.
*A01H 5/08* (2018.01)
*A01H 6/74* (2018.01)

(52) U.S. Cl.
USPC ..... Plt./188
CPC ..... *A01H 6/7454* (2018.05)

(58) Field of Classification Search
USPC ..... Plt./188
CPC ..... A01H 6/7454; A01H 5/08
See application file for complete search history.

*Primary Examiner* — Keith O. Robinson
(74) *Attorney, Agent, or Firm* — Knobbe, Martens, Olson & Bear, LLP

(57) ABSTRACT

The new variety of nectarine tree named 'Sunect30' is characterized by early ripening, circular fruit with a sweet, subacid flavor. The fruit is very large-sized, with firm flesh that is adherent to the stone.

1 Drawing Sheet

Latin name of the genus and species claimed: *Prunus persica* var. *nucipersica*.

Variety denomination: 'SUNECT30'.

BACKGROUND AND SUMMARY OF THE INVENTION

This application relates to the discovery and asexual propagation of a new and distinct variety of nectarine tree, *Prunus persica* var. *nucipersica* cv. 'Sunect30'. The new variety was first originated by hybridization and identified in September 2018 by Terry A. Bacon and Terrence J. Frett as breeder number 'NE2211W'. The new variety was first evaluated by Terry A. Bacon and Terrence J. Frett near Wasco, Calif. in Kern County.

The seed parent is 'NE1362W' (unpatented breeding selection) and the pollen parent is bulk pollen of seven unpatented breeding program selections: 'NE1463W', 'NE1563W', 'NE1568W', 'NE1574W', 'NE1599W', 'NE1642W' and 'NE1661W'. The parent varieties were first crossed in March 2015, the date of first sowing being March 2016 and the date of first flowering being March 2018. The new nectarine variety 'Sunect30' was first asexually propagated by Terry A. Bacon and Terrence J. Frett near Wasco, Kern County, Calif. in February 2019 by dormant grafting.

The new variety 'Sunect30' is characterized by early ripening, circular fruit with a sweet subacid flavor. The fruit is very large-sized, with firm white flesh that is adherent to the stone.

The new variety 'Sunect30' resembles its seed parent 'NE1362W' in that both have fruit with white flesh and showy flowers. However, the new variety 'Sunect30' is distinguished from its seed parent 'NE1362W' in that the fruit of the new variety ripens about 9 days later than that of 'NE1362W'. Further, flowering time for the new variety 'Sunect30' starts 12 days earlier than 'NE1362W', and the new variety 'Sunect30' has a smaller fruit size at 160 g compared to 230 g for 'NE1362W'.

The new variety 'Sunect30' can be distinguished from each of the seven unpatented nectarine varieties of the bulk pollen parent: 'NE1463W', 'NE1563W', 'NE1568W', 'NE1574W', 'NE1599W', 'NE1642W' and 'NE1661W'. The fruit of the new variety 'Sunect30' ripens later than the fruit of each of 'NE1463W', 'NE1563W', 'NE1568W', 'NE1574W', 'NE1642W' and 'NE1661W' and ripens earlier than 'NE1599W'. Further, the new variety 'Sunect30' has a fruit weight of 160 g, compared to a fruit weight of 120 g for 'NE1563W', a fruit weight of 132 g for 'NE1568W', a fruit weight of 140 g for 'NE1574', a fruit weight of 117 g for 'NE1642W', a fruit weight of 170 g for 'NE1463W', a fruit weight of 168 g for 'NE1599W'.

The new variety 'Sunect30' has a Brix:acid of 28 compared to a Brix:acid of 14 for 'NE1463W', 12 for 'NE1563W', 14 for 'NE1568W', 15 for 'NE1574W' 15 for 'NE1599W', 37 for 'NEW1642W', and 16 for 'NE1661W'. The new variety 'Sunect30' has a lower fruit acidity at 0.54 compared to 0.88 for 'NE1463W', 1.1 for 'NE1563W', 0.85 for 'NE1568W', 0.82 for 'NE1574W', 0.91 for 'NE1642W' and 0.87 for 'NE1642'.

Additionally, the flowers of the new variety 'Sunect30' are showy similar to the flowers of 'NE1643W', 'NE1568W' and 'NE1599W'. However, they differ from the non-showy flowers of 'NE1563W', 'NE1574W', 'NE1642W', and 'NE1661W'. Lastly, flowering time for the new variety 'Sunect30' starts later than the flowering time of 'NE1563W', 'NE1568', 'NE1574W' and earlier than 'NE1463W', 'NE1599W', 'NE1642W' and 'NE1661W'.

The new variety 'Sunect30' resembles 'Spring Bright' (U.S. Plant Pat. No. 7,507), 'Sunectwentyone' (U.S. Plant Pat. No. 18,114), and 'Zee Fire' (U.S. Plant Pat. No. 13,501)

in that the fruit of all four varieties ripens in the early season. However, the fruit of the new variety 'Sunect30' has white flesh compared to yellow flesh for the fruit of 'Spring Bright', 'Sunectwentyone' and 'Zee Fire'. The new variety 'Sunect30' resembles that of Candy Pearl (U.S. Plant Pat. No. 14,249) in that the fruit of both varieties has white flesh and both varieties have showy flowers, but the new variety 'Sunect30' blooms 22 days earlier than 'Candy Pearl' and the fruit ripens 33 days earlier than that of 'Candy Pearl'.

The new variety 'Sunect30' has been shown to maintain its distinguishing characteristics through successive asexual propagations by, for example, cuttings and grafting.

BRIEF DESCRIPTION OF THE DRAWING

The accompanying color photographic illustration taken from a 4-year-old plant shows typical specimens of the foliage and fruit of the present new nectarine variety 'Sunect30'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1986.

The descriptive matter which follows pertains to 3-year-old 'Sunect30' plants grown in Wasco, Kern County, Calif., and is believed to apply to plants of the variety grown under similar conditions of soil and climate elsewhere. Observations were made in 2021.

TREE

General: (Measurements were taken on 3-year-old trees unless otherwise noted.).

- *Height*.—Approximately 3.1 m.
- *Size*.—Large. Normal for most nectarine varieties.
- *Spread*.—Normal for most nectarine varieties. Reaches a spread of 5 m with normal vase pruning.
- *Vigor*.—Strong. Approximately 1.5 meters of growth in the first growing season.
- *Growth*.—Semi-upright.
- *Productivity*.—Very productive. About 700, 25-pound cartons per acre on mature trees
- *Bearer*.—On one-year old shoots.
- *Fertility*.—Self-fertile.
- *Hardiness*.—Hardy in all fruit growing areas of California.
- *Disease resistance/susceptibility*.—No specific testing for relative plant disease resistance/susceptibility has been undertaken. Under close observation in Kern County, Calif., no particular plant/fruit disease resistance/susceptibility has been observed.
- *Chilling requirements*.—About 150 hours at or below 7.2° C.
- *Shipping and storage characteristics*.—Excellent for about 5 weeks at 2° C.

Trunk: (Measurements were taken at approximately 30 cm above the soil line.).

- *Diameter*.—Approximately 16 cm.
- *Texture*.—Medium shaggy, increasing with age.
- *Trunk color*.—About medium Greyed-Orange 173A becoming darker with age.

Branches: (Measurements were taken at approximately 90 cm above the soil line.).

- *Size*.—Approximately 12 cm in diameter.
- *Texture*.—Smooth on young wood, increasing roughness with tree age.
- *Color*.—About medium Greyed-Orange 173A becoming darker with age.
- *Lenticels*.—Present.
- *Lenticels numbers*.—Plentiful.
- *Lenticels density*.—Medium, Approximately 1-3 per $cm^2$.
- *Lenticels color*.—About Light Grey 201D.
- *Lenticels length*.—Approximately 3 mm.
- *Lenticels width*.—Approximately 1 mm.

One year old shoots: (Data taken in September at the midpoint of current-season growth.).

- *Size*.—Average diameter approximately 6 mm.
- *Color*.—Topside: About Medium Greyed-Orange 164B. Underside: About Medium Greyed-Orange 164B.
- *Internode length*.—About 2.0 cm, midway on shoot.
- *Lenticels dimensions*.—Very small. Length: About 5 mm. Width: About 1.2 mm.
- *Lenticels*.—Plentiful, about 8/$cm^2$.
- *Lenticels color*.—About Light Grey 201D.
- *Intensity of anthocyanin on upper side of shoots*.—Absent or very sparse.

Vegetative buds: (Data were taken in September at the midpoint of current-season growth.).

- *Position of vegetative bud in relation to shoot*.—Slightly held out.
- *Size*.—Medium, approximately 1.5 mm×2.5 mm.
- *Shape*.—Ovoid.
- *Shape of apex*.—Obtuse.
- *Color*.—About Dark Brown 200B.

Flower buds: (Data were taken in September at the midpoint of current-season growth.).

- *Distribution*.—2 flowers buds per node, on one-year old shoots.
- *Shape*.—Rounded.
- *Dimensions*.—Approximately 4 mm×2.5 mm.
- *Color*.—About Dark Greyed-Orange 165A.
- *Ratio of flower buds to vegetative buds*.—2 flowers buds: 1 vegetative bud.

FOLIAGE

Leaves: (Data taken on fully expanded leaves).

- *Size*.—Medium.
- *Average length*.—Long; approximately 13.0 cm without petiole.
- *Average width*.—Medium; approximately 5.0 cm.
- *Ratio of length to width*.—Moderately elongated, approximately 2.3:1.
- *Shape*.—Lanceolate.
- *Color of upper side*.—About Dark Green 139A.
- *Color of lower side*.—About Medium Green 139B.
- *Glossiness of upper side*.—Medium.
- *Angle at apex* (*excluding tip*).—Acute.

*Shape of base*.—Cuneate.
*Venation*.—Pinnately net veined.
*Vein color*.—About Light Green 139D.
*Surface texture* (*upper and lower*).—Smooth.
*Shape in cross-section*.—Concave.
*Profile*.—Up-folded.
*Leaf blade tip*.—Curved downward.
*Undulation of margin*.—Pronounced.
*Density of pubescence of lower side*.—Absent or very sparse.
*Incisions of margin*.—Crenate.
*Red mid-vein on the lower side of the leaf blade*.—Absent.

Petiole:
*Length*.—Medium; approximately 10 mm.
*Diameter*.—Approximately 3 mm.
*Color*.—About Light Green 139D.

Stipules:
*Number/leaf bud*.—Approximately 2 when present.
*Typical length*.—Medium, approximately 8 mm.
*Color*.—About Dark Greyed-Red 180A when dried.
*Persistence*.—Falls off.

Leaf glands:
*Form*.—Globose.
*Average number and arrangement*.—0-5, usually 4, arranged predominately on upper pedicel and rarely on base of leaf.
*Diameter*.—Approximately 2 mm.
*Color*.—About Medium Greyed-Orange 164C.

FLOWERS

General:
*Time of beginning of flowering*.—Very early for the San Joaquin Valley, Calif.
*Flower blooming period*.—First bloom: Approximately February 2 in Wasco, Calif. Location of First bloom: Toward base of the tree canopy. Full bloom: Approximately February 6 in Wasco, Calif. Location of Full bloom: Central part of the tree canopy.
*Duration of bloom*.—Approximately 10 days.
*Flower diameter*.—Medium, approximately 27 mm.
*Flower form*.—Showy.
*Pollen amount*.—Abundant.

Pedicel:
*Length*.—Long, approximately 10 mm.
*Diameter*.—Approximately 1.5 mm.
*Color*.—About Dark Greyed-Red 180A.
*Pubescence*.—Absent.

Sepals:
*Number*.—5.
*Length*.—Approximately 6 mm.
*Diameter*.—Approximately 4 mm.
*Shape*.—Triangular.
*Color*.—About Medium Red 44A.
*Texture*.—Smooth to slightly bumpy.
*Margins*.—Smooth.
*Position*.—Adpressed to petals.
*Frequency of flowers with double sepals*.—None.

Receptacle:
*Depth*.—Medium, approximately 2 mm.
*Pubescence of inner surface*.—Absent.
*Pubescence of outer surface*.—Absent.

Petals:
*Number*.—5.
*Arrangement*.—Slightly overlapping.
*Color*.—About Light Red 54D.
*Surface texture*.—Smooth.
*Length*.—Long, approximately 13 mm.
*Width*.—Approximately 7 mm.
*Shape*.—Elliptic.
*Apex shape*.—Rounded.
*Base shape*.—Narrows at point of attachment.
*Undulation of margin*.—Medium.
*Frequency of flowers with double petals*.—Never.
*Claw*.—Absent.

Pistil:
*Length*.—Approximately 37 mm.
*Ovary diameter*.—Approximately 1.5 mm.
*Pubescence*.—Absent.
*Stigma extension in comparison to anthers*.—Above.
*Frequency of supplementary pistils*.—Few.

Stamens:
*Number*.—Approximately 32-38. Average 34.
*Length*.—Variable, ranging approximately from 3 mm to 10 mm.
*Filament color*.—About White 155A.
*Pollen color*.—About Medium Red 52A.
*Position*.—Perigynous.

FRUIT

General: (Description taken near Wasco, Kern County, Calif.).
*Time of beginning of fruit ripening*.—Early for the San Joaquin Valley, Calif.
*Harvest*.—
*Date of first pick*.—Approximately May 19.
*Date of last pick*.—Approximately May 28.

Maturity when described: Firm-mature.

Peduncle:
*Length of stem*.—Short, approximately 7 mm.
*Diameter of stem*.—Approximately 5 mm.
*Color of stem*.—About Medium Greyed-Orange 164B.

Size:
*Average size*.—Very large.
*Diameter in line with suture plane*.—Approximately 77 mm.
*Diameter perpendicular to suture*.—Broad, approximately 68 mm.
*Average weight*.—Approximately 160 gm.
*Height*.—Tall, approximately 72 mm.

Shape:
*Viewed from apex*.—Circular.
*In lateral view, perpendicular to suture*.—Circular.
*In-line with suture*.—Circular.
*Symmetry*.—Symmetric or slightly asymmetric.
*Shape of base*.—Depressed.
*Shape of apex*.—Slightly depressed.
*Depth of stalk cavity*.—Medium, approximately 8 mm.
*Width of stalk cavity*.—Medium, approximately 15 mm.
*Depth of suture*.—Shallow.

Skin:
*Thickness*.—Medium, typical of most varieties.
*Adherence to flesh*.—Strong.
*Surface texture*.—Nearly smooth.
*Taste*.—Neutral.

*Reticulation*.—Absent.
*Tendency to crack*.—Rare.
*Pubescence*.—Absent.
*Bloom on skin*.—Absent or very weak.
*Ground color*.—Not visible.
*Relative area of over color of skin*.—Whole surface.
*Overcolor*.—About Dark Red, ranging from Dark Red 53C to Dark Red 53A.
*Pattern of over color of skin*.—Solid.
*Number of lenticels*.—None to a few.
*Size of lenticels*.—Very small approximately 0.5 mm.

Flesh:
*Ripens*.—Evenly.
*Texture*.—Crisp-juicy.
*Color*.—About White 155A with flecks of Dark Red 45B developing as it ripens.
*Flavor*.—Sweet, subacid.
*Firmness*.—Firm, typically 10 lb pressure at harvest.
*Juiciness*.—Medium, able to squeeze free juice easily.
*Acidity*.—Low for nectarines, 0.54% titratable acidity.
*Sweetness*.—Medium.
*Brix*.—Approximately 15% at harvest.
*Adherence of stone to flesh*.—Adherent.
*Fiber*.—Medium.

Stone:
*Stone freeness*.—Cling.
*Stone size*.—Size: Medium. Length: Approximately 28 mm. Diameter in line with suture: Approximately 21 mm. Diameter perpendicular to suture: Approximately 18 mm.
*Stone size in relation to the fruit*.—Medium.
*Color*.—About Light Greyed-Orange 164C.
*Position of maximum diameter*.—Middle.
*Stone shape*.—Lateral view: Medium elliptic. Basal view: Broad elliptic. Ventral view: Broad elliptic.
*Base shape*.—Nearly straight.
*Apex shape*.—Pointed.
*Ridges*.—Rounded throughout.
*Outgrowing keel*.—Well developed.
*Ventrical edge*.—Medium.
*Dorsal edge*.—Full, deep grooves.
*Fibers*.—Retains short fiber-like threads along ridges.
*Symmetry in lateral view*.—Symmetric.
*Texture of lateral surface*.—Rough.
*Width of stalk-end*.—Medium, approximately 4 mm.
*Tendency to split*.—Rare.

What is claimed is:

1. A new and distinct variety of nectarine tree named 'Sunect30' as herein described and illustrated.

* * * * *

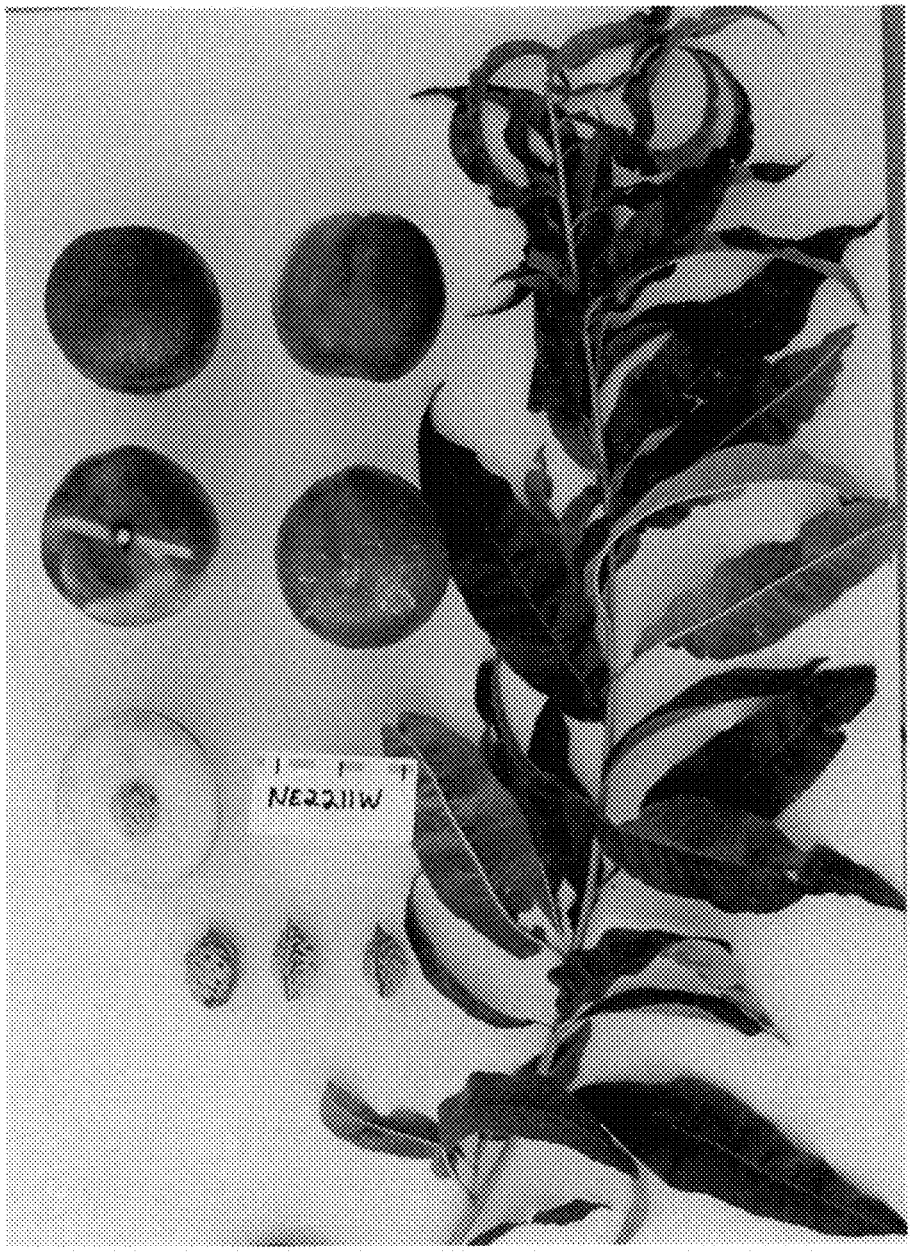
NE2211W